(12) United States Patent
Kimura

(10) Patent No.: US 6,762,840 B1
(45) Date of Patent: Jul. 13, 2004

(54) IMAGE INFORMATION READING APPARATUS DESIGNED TO MAINTAIN LIGHT AMOUNT TO BE DETECTED AT UNIFORM LEVEL

(75) Inventor: Toshihito Kimura, Kaisei-machi (JP)

(73) Assignee: Fuji Photo Film Co., Ltd., Kanagawa-Ken (JP)

(*) Notice: Subject to any disclaimer, the term of this patent is extended or adjusted under 35 U.S.C. 154(b) by 664 days.

(21) Appl. No.: 09/654,169

(22) Filed: Sep. 1, 2000

(30) Foreign Application Priority Data

Sep. 3, 1999 (JP) .......................................... 11-250450

(51) Int. Cl.[7] .............................................. G01N 21/64
(52) U.S. Cl. .................................... 356/417; 250/458.1
(58) Field of Search ........................ 356/344; 250/458.1, 250/459.1, 461.1, 461.2; 204/612

(56) References Cited

U.S. PATENT DOCUMENTS 5,108,179 A * 4/1992 Myers ......................... 356/344
5,207,880 A * 5/1993 Middendorf et al. ........ 204/612
5,242,567 A * 9/1993 Fujimiya et al. ............. 356/344
5,459,325 A * 10/1995 Hueton et al. .............. 356/344
5,900,640 A   5/1999 Ogura

FOREIGN PATENT DOCUMENTS

JP          10-3134           1/1998

* cited by examiner

Primary Examiner—Zandra Smith
(74) Attorney, Agent, or Firm—Sughrue Mion, PLLC

(57) ABSTRACT

An image information reading apparatus of the optical head scanning type is designed to maintain the light amount to be detected at an uniform level while an optical head shifts its scanning position. A sample 10 is irradiated with a laser beam L by an optical head 50 and fluorescence K emitted by the sample 10 is led to a PMT 40, wherein the fluorescence K proceeding toward the PMT 40 as a diverging beam is refracted by a collective lens 90 located in the optical path between the optical head 50 and the PMT 40 so that the beam of the fluorescence K enters the PMT 40 with a contracted beam diameter.

8 Claims, 3 Drawing Sheets

F I G . 1
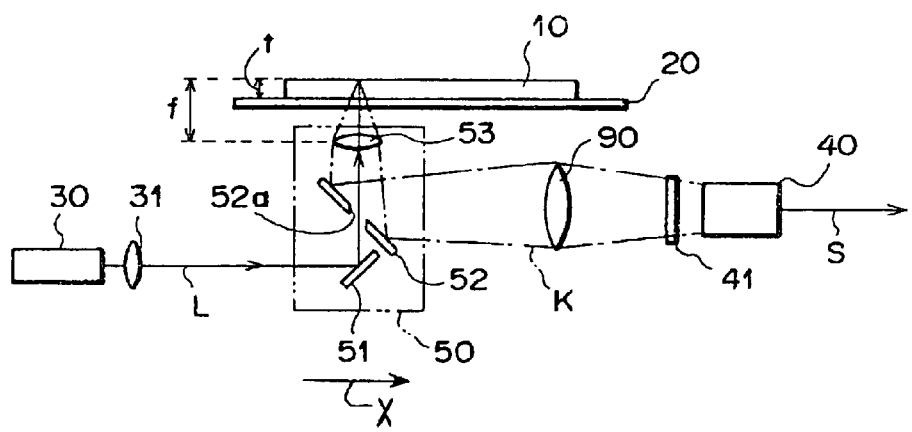

IMAGE INFORMATION READING APPARATUS DESIGNED TO MAINTAIN LIGHT AMOUNT TO BE DETECTED AT UNIFORM LEVEL

BACKGROUND OF THE INVENTION

1. Field of the Invention

The present invention relates to an image information reading apparatus, and more specifically, relates to an image information reading apparatus provided with an optical head which is capable of moving at least in a primary scanning direction.

2. Description of the Related Art

A fluorescence detection system adopting fluorescent dye as a marker has been well-known in the fields of biochemistry and molecular biology. With this system, fluoroscopic image information of a sample, e.g. a gel-like sample supporting an organic substance which is distributed therein and marked with the fluorescent dye, can be read in a photoelectric manner. That enables, for example, evaluation of gene sequences, a level of gene expression, paths and stages of a metabolic process, an absorption process or an excretion process of a substance administered to a rat for an experiment, and molecular weight and other properties of a protein, as well as separation and identification of a protein.

Further, molecular weight and other properties of a DNA fragment may also be evaluated by preparing a gel-like supporting object in which a plurality of the DNA fragments marked with the fluorescent dye are distributed based on electrophoresis, a phenomenon in which living cells in a suspension or molecules of a biological compound (e.g. a protein) in a solution are collected around an anode or a cathode because of interaction between electrical charges carried by the cells or the molecules and an electric field in the suspension or the solution, irradiating the gel-like supporting object with stimulating light which is capable of stimulating the fluorescent dye used as the marker therein, photoelectrically detecting the fluorescence induced in the gel-like supporting object to obtain image information representing the distribution of the DNA fragments marked with the fluorescent dye, and displaying a visual image (an image of the above distribution which may be referred to as a fluoroscopic image) on a display device such as a display part of CRT based on the obtained image information, wherein the gel-like supporting object may be prepared by adding the fluorescent dye to a solution containing the DNA fragments and then inducing electrophoresis motion of the DNA fragments within the gel-like supporting object, by inducing the electrophoresis motion of the DNA fragments within the gel-like supporting object containing the fluorescent dye, or by inducing the electrophoresis motion of the DNA fragments within the gel-like supporting object and then soaking the gel-like supporting object under a solution containing the fluorescent dye.

An image information reading apparatus for carrying out the processes as described above has become quite popular in the fields of biochemistry and molecular biology. This image information reading apparatus irradiates the gel-like supporting object with the stimulating light, detects the fluorescence in the photoelectric manner to obtain the image information, and displays the fluoroscopic image on the display device based on the obtained image information.

Though the sample is scanned with the stimulating light using a rotating polygon mirror and an fθ lens in the image information reading apparatus of the most popular type, the image information reading apparatus suggested in the present application is of another type called an optical head scanning type which does not employ the rotating polygon mirror and the fθ lens. FIGS. 4 and 5 illustrate a typical constitution of the image information reading apparatus of the optical head scanning type which appears in, for example, Japanese Patent Publication No. 10(1998)-3134. The illustrated apparatus is constituted of a light source 30 for generating an stimulating light beam L, a lens 31, a photomultiplier 40 for detecting intensity of fluorescence K entering thereon in the photoelectric manner to generate an image signal S, an stimulating light cutting filter 41, a sample holding portion 20 for holding a scanning target carrying certain image information, a gel-like supporting object 10 with glass in this example, an optical head 50 which leads the stimulating light beam L emitted by the light source 30 to the gel-like supporting object 10 placed on the sample holding portion 20 so that the gel-like supporting object 10 is irradiated with the stimulating light beam L and the fluorescence K is induced thereby and which leads the fluorescence K emitted downward from the upper surface of the gel-like supporting object 10 to the photomultiplier 40, primary scanning means 60 for moving the optical head 50 in a primary scanning direction (a direction of x as indicated with an arrow in FIG. 4) with respect to the gel-like supporting object 10 so that the gel-like supporting object 10 is scanned in the primary scanning direction with the stimulating light beam L led thereto by the optical head 50, and secondary scanning means 80 for moving the optical head 50 etc. in a secondary scanning direction (a direction of Y as indicated with another arrow in FIG. 4) which is orthogonal to the primary scanning direction.

According to the image information reading apparatus of the optical head scanning type, the stimulating light beam L passes through an aperture 52a opened on the mirror 52 which constitutes the optical head 50, and then stimulates the gel-like supporting object 10 to induce the fluorescence K therein. The fluorescence K emitted downward from the upper surface of the gel-like supporting object 10 proceeds along an optical path of the stimulating light beam L in the reverse direction and reaches the mirror 52 on which the aperture 52a is opened. As a beam diameter of the fluorescence K at the mirror 52 is larger than that of the stimulating light beam L, only a small fraction of the fluorescence K passes through the aperture 52a, and a major portion of the fluorescence K is reflected by the mirror 52, led to the photomultiplier 40, and detected by the photomultiplier 40 in the photoelectric manner. The image information reading apparatus of the optical head scanning type is effective in improving an S/N ratio of the signal (the image information) read in the photoelectric manner, as the apparatus does not employ a dichroic mirror for irradiating the scanning target, e.g. the gel-like supporting object 10, and thus provides more excitation energy to the scanning target. than an apparatus in which the scanning target is irradiated with the stimulating light beam reflected by the dichroic mirror. In addition, sharpness of the image information may also be improved as the image information reading apparatus of the optical head scanning type detects only the fluorescence induced at a spot currently irradiated with the stimulating light beam and does not detect afterglow of the fluorescence from adjacent areas where the irradiation has already been completed.

However, the image information reading apparatus of the optical head scanning type also has a problem. The problem occurs because the scanning target which carries the image information to be read may be any of a gel-like supporting object without glass, a membrane filter onto which the gel-like supporting object is transcribed, or an accumulation phosphor sheet, instead of the gel-like supporting object with glass described above. Though the fluorescence would be emitted from the upper surface of the scanning target as shown in FIG. 5 if the scanning target was the gel-like supporting object with glass, the fluorescence might be emitted from other parts in the scanning target if the scanning target was one of the other types listed above.

For example, the fluorescence would be emitted from any part along a thickness dimension of the scanning target if the scanning target was the gel-like supporting object without glass, or would be emitted from a lower surface of the scanning target if the scanning target was the accumulation phosphor sheet. Concerning the membrane filter, the fluorescence is emitted from a lower surface thereof the same as the accumulation phosphor sheet. Moreover, though a major portion of the fluorescence emitted from the accumulation phosphor sheet etc. originates from the lower surface thereof, the surface which corresponds to a plane of incidence for the stimulating light beam, a small fraction of the fluorescence may be emitted from planes above the lower surface.

Thus, as illustrated in FIG. 6, a distance f between a light-emitting plane of the scanning target 10 and an objective lens 53 provided in the optical head 50 may vary when the type or thickness t of the scanning target 10 is changed. For this variation of f, the objective lens 53 fails to sufficiently collimate emitted light K, e.g. the fluorescence, emitted from the light-emitting plane of the scanning target 10. Finally, the emitted light K reaches the photomultiplier 40 as diverging light (especially when the distance f between the objective lens and the light-emitting plane is shorter than a focal length f0 of the objective lens).

As the amount of light incident on the photomultiplier 40 varies according to distance between the optical head 50 and the photomultiplier 40, the amount of light detected by the photomultiplier 40 may change when a scanning position of the optical head 50 is shifted even if the original light amount emitted by the scanning target remains constant, which may cause a problem of non-uniform density in the image information S.

Besides, uniformity of the density of the image information S would be further deteriorated if the scanning target 10 was one which emits the fluorescence at any part along the thickness dimension thereof, e.g. the gel-like supporting object without glass, as thickness of a certain portion of the scanning target, the portion from which detectable fluorescence is emitted, would change as the scanning position of the optical head is shifted.

SUMMARY OF THE INVENTION

The object of the present invention is to provide an image information reading apparatus of the optical head scanning type, which is designed to maintain the amount of detected light originating from a scanning target of any thickness and any type at an uniform level when the scanning position of the optical head is shifted.

To attain this object, the image information reading apparatus of the present invention is provided with an optical element which is capable of collecting light, e.g. a collective lens, between an optical head and photoelectric reading means thereof in order to compensate for a gap between a focal length of an objective lens of the optical head and a distance between a reading plane of the scanning target and the objective lens, this gap perhaps being caused because of the scanning target having a thickness different from a predetermined thickness.

The image information reading apparatus of the present invention is constituted of a light source for emitting a light beam, the photoelectric reading means for detecting intensity of incident light in an photoelectric manner, a sample holding portion for holding the scanning target carrying certain image information, the optical head which leads the light beam emitted by the light source to the scanning target placed on the sample holding portion so that the scanning target is irradiated with the light beam and which leads induced light emitted by the scanning target in response to the irradiation thereon to the photoelectric reading means, primary scanning means for moving the optical head in one direction (a primary scanning direction) with respect to the scanning target so that the scanning target is scanned in the primary scanning direction with the light beam led thereto by the optical head, secondary scanning means for moving at least one of the optical head or the sample holding portion in another direction (a secondary scanning direction) which is substantially orthogonal to the primary scanning direction, and the optical element which is provided at a part on an optical path of the induced light between the optical head and the photoelectric reading means and which has a sufficient refractive power for collecting the induced light led toward the photoelectric reading means by the optical head.

The sample holding portion includes a sample table etc. for holding the scanning target as a main constituent thereof. Whatever constitution the sample holding portion may have, any of the gel-like supporting object, the membrane filter onto which the gel-like supporting object is transcribed, the gel-like supporting object with glass, a slide glass, a microtiter plate, the accumulation phosphor sheet or another similar sample used in the fields of biochemistry and molecular biology can be adopted as the scanning target. Accordingly, one example of the scanning target carrying the certain image information may be the gel-like supporting object in which the organic substance marked with the fluorescent dye is distributed.

The term "organic substance" as used herein refers to any substance related to organisms and covers any substance which may act as a hormone, a tumor marker, an enzyme, protein, nuclear acid, antibody or antigen, and cDNA and mRNA of any kind.

The term "induced light" as used herein refers to any kind of light emitted by the scanning target in response to the irradiation and covers simple reflected light, the fluorescence induced therein, light induced by any type of stimulation, etc. The light beam with which the scanning target is irradiated may be a beam of simple illumination light, or may be a beam of stimulating light, e.g. a laser beam, which is capable of stimulating a simple phosphor or a phosphor which emits light under certain stimulation.

It is desirable to have the secondary scanning means capable of moving the optical head, and have the optical element constituted of at least a first optical element to be moved together with the optical head by the secondary scanning means and a fixed second optical element. This is because the level of the light amount to be detected can be made even more uniform over all of the scanning positions of the optical head when a plurality of optical elements are used.

The optical element used in the present invention may be a lens with a positive refractive power, a parabolic mirror, a concave mirror, etc. The photoelectric reading means in the present invention is preferably, but not limited to, a photomultiplier or a similar device which is capable of detecting the induced light emitted from the scanning target with high sensitivity, wherein it is also possible to adopt well-known photoelectric reading means of another kind such as a cooled CCD.

According to the image information reading device of the present invention, the light amount of the induced light incident on the photoelectric reading means may be maintained at a substantially uniform level regardless of the scanning position of the optical head, by providing the optical element between the optical head and the photoelectric reading means in order to compensate for the gap between the focal length of the objective lens in the optical head and the distance between the light-emitting plane of the scanning target and the objective lens, the gap which may be produced when the thickness or the type of the scanning target is different from the predetermined one.

BRIEF DESCRIPTION OF THE DRAWINGS

FIG. 1 is a side view of the image information reading apparatus of the present invention in accordance with the first embodiment which has a relatively simple structure.

DESCRIPTION OF THE PREFERRED EMBODIMENTS

Figure 2:
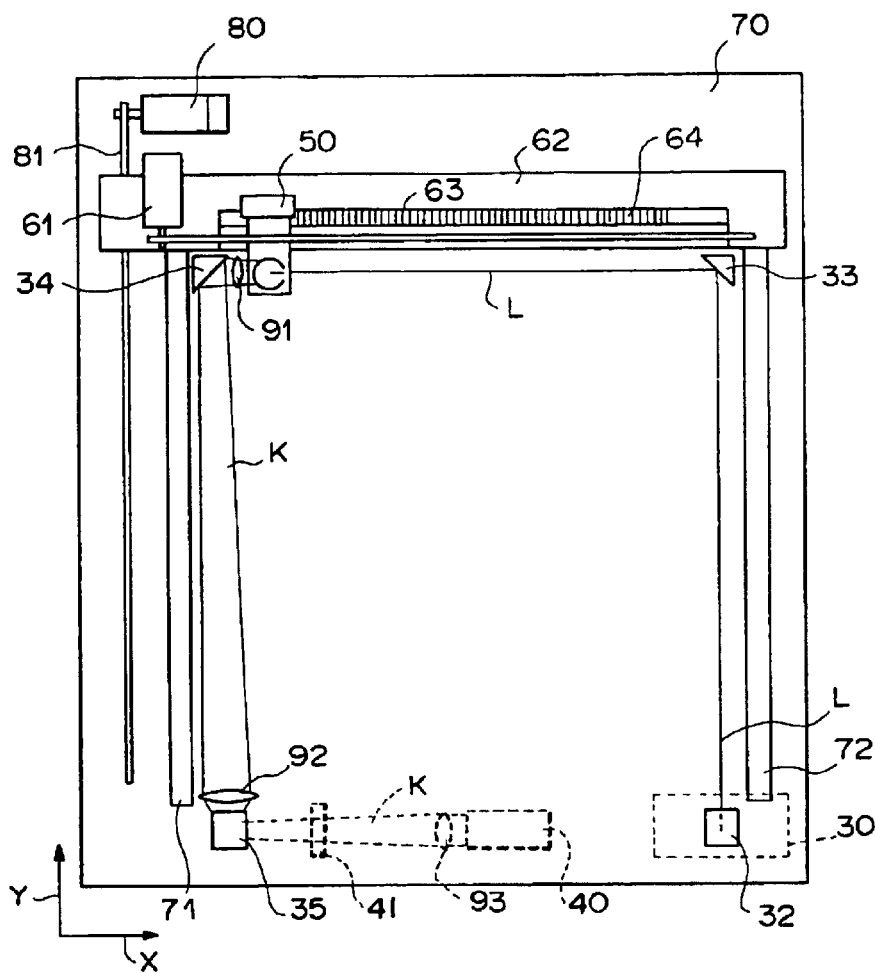
FIG. 2 is an upper view of the image information reading apparatus of the present invention in accordance with the second embodiment which has more complex structure than the image information apparatus of FIG. 1.

The first embodiment of the image information reading apparatus of the present invention will now be described with reference to FIG. 1 of the accompanying drawings.

The image information reading apparatus of FIG. 1 is constituted of a sample table 20 which is transparent and which is fixed at a certain height with a scanning target 10 placed thereon, wherein the scanning target 10 contains an organic substance which is marked with fluorescent dye and distributed therein, a laser 30 for generating a laser beam L of a suitable wavelength for stimulating the fluorescent dye, a lens 31 for collimating the laser beam L emitted by the laser 30, a photomultiplier (hereinafter called PMT) 40 for photoelectrically detecting fluorescence K emitted by the fluorescent dye stimulated within the scanning target 10, an optical head 50 which leads the laser beam L to the scanning target 10 placed on the sample table 20 so that the scanning target 10 is irradiated with the laser beam L and the fluorescence K is induced thereby and which leads the fluorescence K emitted by the scanning target 10 to the PMT 40, a laser beam cutting filter 41 provided at a part on an optical path between the optical head 50 and the PMT 40, a collective lens 90 which is provided at another part on the optical path between the optical head 50 and the PMT 40 and which has sufficient refractive power for collecting the florescence K led toward the PMT 40 by the optical head 50, primary scanning means (not shown) for moving the optical head 50 at a constant speed in a direction of X as indicated with an arrow in FIG. 1, and secondary scanning means (not shown) for moving the laser 30, the optical head 50, the laser beam cutting filter 41, the collective lens 90 and the PMT 40 all together in a normal direction of the figure (a direction which is orthogonal to the direction of X).

In this embodiment, the laser 30 is fixed so that the laser beam L is emitted thereby in the direction of X, and the PMT 40 is fixed so that the fluorescence K proceeding in the direction of X is appropriately detected thereby.

The optical head 50 is constituted of a plane mirror 51 for reflecting the collimated laser beam L so that a direction of an optical path thereof which originally corresponds to the direction of X is folded upward into a direction orthogonal to a surface of the scanning target 10, an aperture-opened mirror 52 on which an aperture 52a is opened, wherein the aperture 52a is relatively small but has a sufficient diameter for letting the reflected laser beam L through, and which reflects a major portion of the fluorescence K emitted downward by the scanning target so that a direction of an optical path thereof is folded into the direction of X, and an objective lens 53 for collecting a beam of the fluorescence K emitted by the scanning target as a diverging beam into a substantially collimated beam.

The objective lens 53 provided within the optical head 50 is a lens which projects an image of an object plane displaced from the objective lens 53 by its focal length f0 onto a plane at infinity, i.e. the lens which precisely collimates the fluorescence K emitted from a plane displaced from the objective lens 53 by the focal length f0, the plane corresponding to an upper surface of the scanning target 10 in FIG. 1. A position of the objective lens 53 is determined assuming the scanning target 10 to be a gel-like supporting object with glass which has a thickness of t0 and emits the fluorescence K from the upper surface thereof. In other words, the optical head 50 has been preset so as to realize the distance equal to f0 between the objective lens 53 and the upper surface of a gel-like supporting object 10' with glass placed on the sample table 20 when the gel-like supporting object 10' has the thickness of t0. Thus, if the scanning target 10 placed on the sample table 20 has a thickness t which is different from the value of t0, a distance f between the upper surface of the scanning target 10 and the objective lens 53 also takes a value different from the value f0 and the objective lens 53 fails to sufficiently collimate the beam of the fluorescence K emitted from the upper surface of the scanning target 10. Especially when f0>f, the beam of the fluorescence K reaches the PMT 40 as a diverging beam.

There are some cases where the beam of the fluorescence k may reach the PMT 40 as a diverging beam even if the thickness of the scanning target 10 is equal to t0. This may occur, for example, when the scanning target 10 is the accumulation phosphor sheet which emits the fluorescence K from a lower surface thereof, as the distance f between a light-emitting plane and the objective lens 53 becomes smaller than the focal length f0 when the scanning object of such a type is selected.

The laser beam cutting filter 41 is a bandpass filter designed to pass the fluorescence K but block the laser beam L in order to prevent any portion of the laser beam L from entering the PMT 40, the portion which may be dispersed or reflected by the scanning target 10 or the sample table 20 and led toward the PMT 40 together with the beam of the fluorescence K.

The operation of the image information reading apparatus of the present embodiment will now be described for the case where the scanning target 10 placed on the sample table 20 emits the fluorescence K from the upper surface thereof but has the thickness t different from the value of t0.

To begin with, the primary scanning means (not shown) conducts a primary scanning process by moving the optical head 50 at the constant speed in the direction of X. The laser 30 constantly emits the laser beam L in the direction of X throughout the primary scanning process, and the laser beam L enters the optical head 50 after being collimated by the lens 31. Then, the laser beam L is reflected upward by the plane mirror 51, passes through the aperture 52a on the aperture-opened mirror 52, passes the objective lens 53, and reaches the scanning target 10 placed on the sample table 20 to irradiate a fractional area thereon.

If the fractional area irradiated with the laser beam L contained the organic substance marked with the fluorescent dye, the fluorescent dye would be stimulated by the laser beam L and the fluorescence K would be induced. On the other hand, if the fractional area did not contain the organic substance, the fluorescence K would not be induced.

Figure 6:
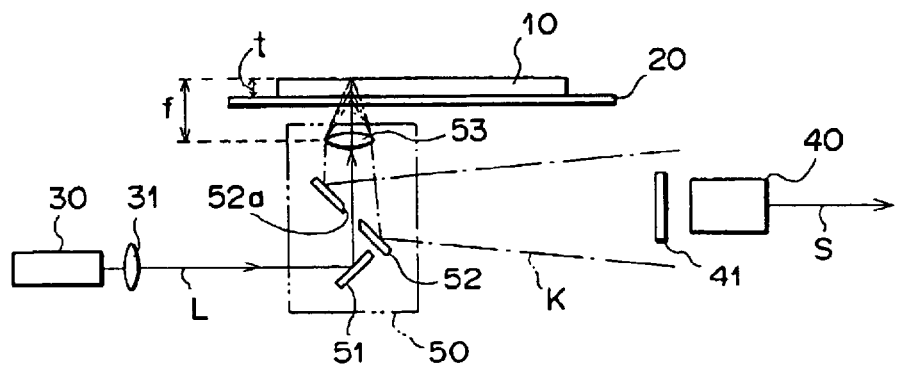
FIG. 6 is a side view of the image information apparatus of FIG. 4 illustrating a potential problem thereof.

After the fluorescence K is induced in the fractional area containing the organic substance, the fluorescence K is propagated into surrounding areas and is sent out to a lower side of the scanning target 10 as a diverging beam emitted from the upper surface of the scanning target 10. The beam of the fluorescence K sent out to the lower side of the scanning target 10 is then collected by the objective lens 53 of the optical head 50 into a downward beam having a diameter larger than the laser beam L. However, the objective lens 53 fails to collimate the beam of the fluorescence K sufficiently because the distance f between the objective lens 53 and the upper surface of the scanning target 10 is smaller than the focal length f0, and the beam of the fluorescence K after passing the objective lens 53 still proceeds as a diverging beam, i.e. the beam diameter of the beam of the fluorescence K grows larger as the beam proceeds away from the objective lens 53. Then the beam of the fluorescence K reaches the aperture-opened mirror 52. Though a small fraction of the beam passes through the aperture 52a and goes downward, the major portion of the beam is reflected on a reflection surface of the aperture-opened mirror 52 and proceeds in the direction of X as the diameter of the aperture 52a is much smaller than the diameter of the beam of the fluorescence K. The diameter of the beam of the fluorescence K grows even larger as the beam proceeds in the direction of X. If the beam diameter keeps on growing at the same rate, the beam will reach the PMT 40 with the beam diameter larger than a detecting aperture of the PMT 40, and the PMT 40 will fail to detect an entire portion of the fluorescence K in the photoelectric manner (see FIG. 6), which means that there will be a loss in the light amount to be detected thereby. Moreover, the amount of the loss changes as a primary scanning position of the optical head 50 is shifted and an electric signal (image signal) S of high accuracy cannot be generated, because the amount of the loss depends on the diameter of the beam of the fluorescence K at the point where the beam reaches the PMT and the above diameter of the beam is proportional to a distance between the optical head 50 and the PMT 40.

The image information reading apparatus of the present embodiment overcomes the problem described above by collecting the diverging beam of the fluorescence K using the collective lens 90 having the sufficient refractive power which is provided in the optical path between the optical head 50 and the PMT 40. The beam of the fluorescence K passes the laser beam cutting filter 41 after being collected by the collective lens 90, and then substantially the entire portion of the beam enters the detection aperture of the PMT 40.

Though a certain portion of the laser beam L emitted for irradiating the scanning target 10 may be dispersed or reflected by the scanning target 10 or the sample table 20 and led toward the PMT 40 together with the beam of the fluorescence K, such a portion of the laser beam L is blocked by the laser beam cutting filter 41 located in the optical path thereof and never reaches the PMT 40.

The fluorescence K incident on the PMT 40 is amplified and detected in the photoelectric manner by the PMT 40, and finally read out as the corresponding image signal S.

The optical head 50 is moved constantly in the direction of X by the primary scanning means throughout the operation described above, and each image signal S generated by the PMT 40 is associated with the corresponding primary scanning position of the optical head 50, i.e. with the corresponding fractional area on the scanning target 10 irradiated with the laser beam L.

After the primary scanning means completes one primary scanning process for the scanning target 10 all the way along the direction of X, the secondary scanning means moves the laser 30, the optical head 50, the collective lens 90, the laser beam cutting filter 41 and the PMT 40 all together in the normal direction of the figure by a small interval (a secondary scanning process), and then another primary scanning process is performed in the same way as described above. As a matter of course, the secondary scanning process is not necessarily performed after one primary scanning process is completed and may be performed simultaneously with the primary scanning process.

Eventually, the entire surface of the scanning target 10 is irradiated with the laser beam L through a combination of the primary scanning processes and the secondary scanning processes to obtain a plurality of the image signals S each associated with one of the fractional areas on the scanning target 10, i.e. to obtain the image information describing how the organic substance marked with the fluorescent dye is distributed in the scanning target 10.

According to the image information reading apparatus of the present embodiment, in summary, even if the scanning target 10 has the thickness t which is different from the predetermined thickness t0 and thus there is a gap between the focal length f0 of the objective lens 53 of the optical head 50 and the distance f between the reading plane (the upper surface in the present embodiment) of the scanning target 10 and the objective lens 53, the gap may be compensated by means of the collective lens 90 provided in the optical path between the optical head 50 and the PMT 40, and the amount of the fluorescence K incident on the PMT 40 may be maintained at a substantially uniform level regardless of the scanning position of the optical head 50.

Though it has been described that the secondary scanning means in the image information reading apparatus of the present embodiment moves the laser 30, the optical head 50, the collective lens 90, the laser beam cutting filter 41 and the PMT 40 all together in the normal direction of the figure, the secondary scanning means may move the sample table 20 in the reverse direction of the normal direction instead, or otherwise, may be designed to move only the optical head 50 and a collective lens 91 (described below) in the same manner as the image information reading apparatus of the second embodiment described below, keeping the laser 30, the laser beam cutting filter 41 and the PMT 40 fixed.

Now, the second embodiment of the image information apparatus will be described with reference to FIG. 2 and FIG. 3 of the accompanying drawings. The image information apparatus described below has a more complex structure than that of the first embodiment. A sample table 20 and a sample 10 to be placed thereon are not shown in FIG. 2.

The image information reading apparatus of the second embodiment is constituted of a fixed base plate 70, a laser 30 for generating the laser beam L, a PMT 40 for detecting the fluorescence K in the photoelectric manner, a sample table 20 which is fixed above the base plate 70, a primary scanning plate 62 which is located between the base plate 70 and the sample table 20 and which is capable of moving in a direction of Y as indicated with an arrow in FIG. 2 (a secondary scanning direction), an optical head 50 which is capable of moving in the direction of Y together with the primary scanning plate 62 and concurrently capable of sliding on the scanning plate 62 in a direction of X as indicated with another arrow in FIG. 2 (a primary scanning direction), the direction which is parallel to a longer length dimension of the primary scanning plate 62 and which is substantially orthogonal to the secondary scanning direction, a primary scanning motor 61, a primary scanning screw 64 and a primary scanning rail 63 for moving the optical head 50 at a constant speed in the primary scanning direction, a secondary scanning motor 80, a secondary scanning screw 81 and secondary scanning rails 71 and 72 for moving the primary scanning plate 62 at a constant speed in the secondary scanning direction, a first mirror 32 fixed on the base plate 70 and a second mirror 33 fixed on the primary scanning plate 62 for leading the laser beam L generated by the laser 30 to the optical head 50 on the primary scanning plate 62, a third mirror 34 fixed on the primary scanning plate 62 and a fourth mirror 35 and a fifth mirror 36 each fixed on the base plate 70 for leading the beam of the fluorescence K from the optical head 50 to the PMT 40, a laser beam cutting filter 41 located at a part on an optical path of the beam of the fluorescence K between the fifth mirror 36 and the PMT 40, a first collective lens 91 fixed on the primary scanning plate 62 at a part on the optical path of the fluorescence K between the optical head 50 and the PMT 40, and a second collective lens 92 and a third collective lens 93 each fixed on the base plate 70 at a part on the optical path of the beam of the fluorescence K between the optical head 50 and the PMT 40.

Figure 3:
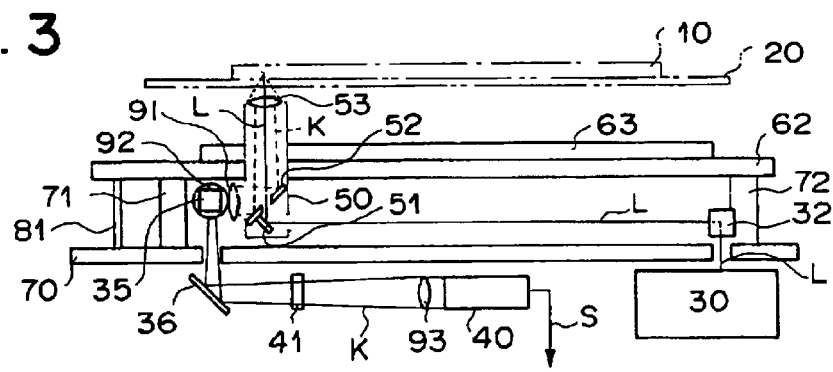
FIG. 3 is a side view of the image information reading apparatus of FIG. 2.
Figure 4:
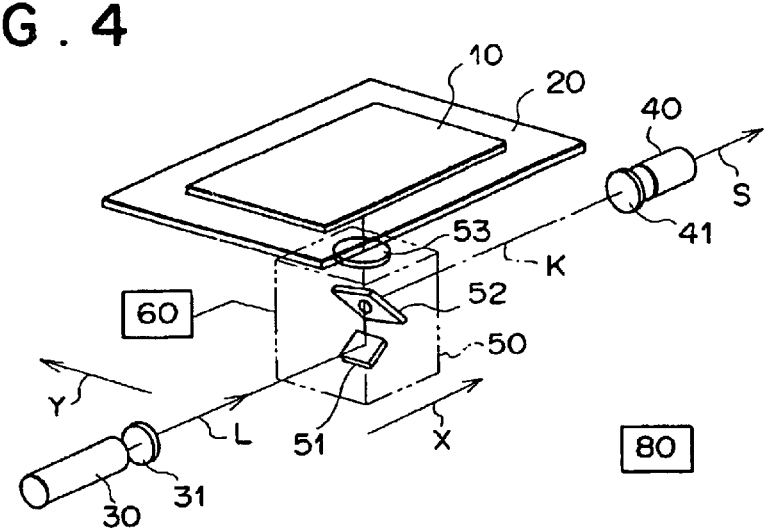
FIG. 4 is a perspective view of a conventional image information reading apparatus of the optical head scanning type.
Figure 5:
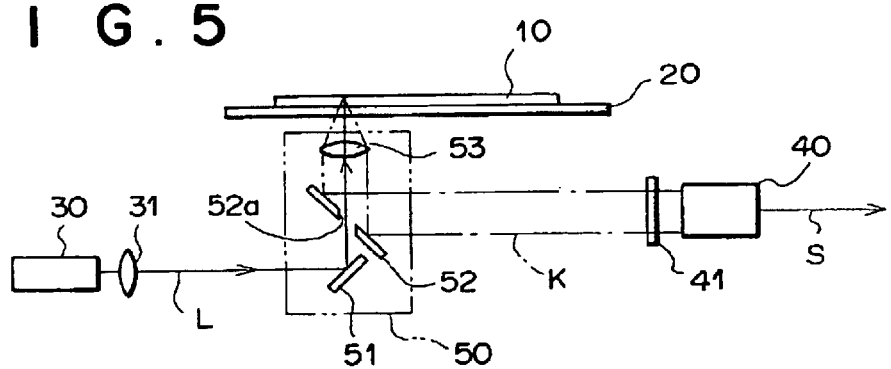
FIG. 5 is a side view of the image information reading apparatus of FIG. 4.

In FIG. 2 and FIG. 3, an element which has a structure and a function equivalent to any of the elements appearing in the image information reading apparatus of the first embodiment is labeled with the identical number, and explanation for such elements is not repeated below.

The secondary scanning rails 71 and 72 which are provided on the base plate 70 extend in the direction of Y, and the secondary scanning motor 80 rotates to turn the secondary scanning screw 81 so that the primary scanning plate 62 engaging with the secondary scanning screw 81 moves in the secondary scanning direction guided by the secondary scanning rails 71 and 72.

Likewise, the primary scanning rail 63 which is provided on the primary scanning plate 62 extends in the direction of X, and the primary scanning motor 61 rotates to turn the primary scanning screw 64 so that the optical head 50 engaging with the primary scanning screw 64 moves in the primary scanning direction guided by the primary scanning rail 63.

The first collective lens 91 fixed on the primary scanning plate 62 may be a convex lens with a focal length of f1=800 mm and a diameter of D1=50 mm, the second collective lens 92 may be a convex lens with a focal length of f2=250 mm and a diameter of D2=50 mm, and the third collective lens 93 may be a convex lens with a focal length of f3=25 mm and a diameter of D3=20 mm.

An objective lens 53 of the optical head 50 may be a convex lens with a focal length of f0=20 mm and a diameter of D0=15 mm, an aperture-opened mirror 52 of the optical head 50 may have a size of 30 mm×20 mm, and an aperture 52a opened thereon may have a diameter of D=4 mm.

The optical head 50 has been preset so that the objective lens 53 keeps a distance equal to the focal length f0 thereof from the upper surface of the sample 10 placed on the sample table 20, assuming that the sample 10 would emit the fluorescence K from the upper surface thereof. However, described below is the operation of the apparatus in the case where a sample which emits the fluorescence K from any part along a thickness dimension thereof, e.g. a gel-like supporting object without glass, is placed on the sample table 20 as the sample 10 to be analyzed.

First of all, the secondary scanning motor 80 rotates to turn the secondary scanning screw 81 so that the primary scanning plate 62 is brought to an initial position thereof, i.e. to an upper movable limit thereof as shown in FIG. 2. Similarly, the primary scanning motor 61 rotates to turn the primary scanning screw 64 so that the optical head 50 is brought to a leftmost movable limit thereof as shown in FIG. 2.

Then, the primary scanning motor 61 rotates in the opposite direction so that the primary scanning screw 64 turned thereby leads the optical head 50 in the direction of X.

Concurrently with the above process, the laser beam L is emitted by the laser 30, is reflected by the first mirror 32 and the second mirror 33, reaches the optical head 50, reflected upward by a mirror 51 of the optical head 50 as shown in FIG. 3, passes through the aperture 52a on the aperture-opened mirror 52, passes the objective lens 53, and irradiates a fractional area on the sample (the gel-like supporting object with glass) 10 placed on the sample table 20.

If the organic substance marked with the fluorescent dye resided in any part along the thickness dimension of the fractional area irradiated with the laser beam L, the laser beam L would stimulate the fluorescent dye and the fluorescence K would be induced thereby. Otherwise, if the organic substance did not reside in the fractional area, the fluorescence K would not be induced therein.

After the fluorescence K is induced at a part in the fractional area where the organic substance resides, the fluorescence K is propagated into surrounding areas thereof and is sent out of the sample 10 as a diverging beam. The beam of the fluorescence K sent out of the sample 10 is then collected by the objective lens 53 into a downward beam having a diameter larger than that of the laser beam L. However, if the distance f between the objective lens 53 and the light-emitting plane of the sample 10 differed from the focal length f0 of the objective lens 53 (especially if f was smaller than f0), the objective lens 53 would fail to collimate the beam of the fluorescence K sufficiently and the beam of the fluorescence K after passing the objective lens 53 would keep proceeding as a diverging beam. The beam diameter of the beam of the fluorescence K grows larger as the beam proceeds away from the objective lens 53. Then the beam of the fluorescence K reaches the aperture-opened mirror 52 of the optical head 50 where a major portion of the beam is reflected on a reflection surface thereof and sent out of the optical head 50.

After being sent out of the optical head 50, the diverging beam of the fluorescence K enters the first collective lens 91 fixed on the primary scanning plate 62, the collective lens with which additional collimation is attempted. Then the beam collected into a nearly-collimated beam by the first collective lens 91 is reflected by the third mirror 34, which is also fixed on the primary scanning plate 62.

Following the reflection, the beam of the fluorescence K enters the second collective lens 92 fixed on the base plate 70 and further collimation is attempted. Then the beam is reflected in a downward direction of FIG. 2 by the fourth mirror 35, and is reflected toward the PMT 40 by the fifth mirror 36.

The beam of the fluorescence K reflected by the fifth mirror 36 then goes through the laser beam cutting filter 41, is collected by the third collective mirror 93, and enters the PMT 40 which converts the incident beam of the fluorescence K into an electrical signal (image signal) S corresponding to the intensity of the beam for output.

When one of the primary scanning processes conducted by the primary scanning motor 61 and the primary scanning screw 64 is completed and the optical head 50 reaches a rightmost movable limit in FIG. 2, the secondary scanning motor 80 turns the secondary scanning screw 81 to move the primary scanning plate 62 in the reverse direction of Y (the downward direction in FIG. 2) by a small interval. Then another primary scanning process is performed with the primary scanning motor 61 rotated in a direction opposite to that of the previous primary scanning process so that the optical head is eventually led to the leftmost movable limit (two-way scanning).

Finally, the entire surface of the sample 10 is irradiated with the laser beam L through a combination of the primary scanning processes and the secondary scanning processes to obtain a plurality of the image signals S each associated with one of the fractional areas on the sample 10, i.e. to obtain the image information describing how the organic substance marked with the fluorescent dye is distributed in the sample 10.

According to the image information reading apparatus of the present embodiment, even if the distance t between the lower surface of the sample 10 and the light-emitting plane where the fluorescence K is induced differs from the predetermined distance (e.g. the thickness between the upper surface and the lower surface of the sample 10) t0, the difference may be compensated by means of the collective lenses 91, 92 and 93 each located at a part on the optical path between the optical head 50 and the PMT 40, and the amount of the fluorescence K incident on the PMT 40 may be maintained at a substantially uniform level regardless of the scanning position of the optical head 50.

Though the collective lenses 91, 92 and 93 act as the optical elements for collecting the beam of the florescence K with sufficient refractive powers in the image information reading apparatus of the present embodiment, optical elements of other types may substitute for these lenses 91, 92 and 93. For example, the collective lens 91 and the mirror 34 may be replaced with a single concave mirror (or parabolic mirror) which has a sufficient refractive power for collecting the fluorescence K and which concurrently acts as a reflective mirror. The collective lens 92 and the mirror 35 may also be replaced with a similar concave mirror etc.

In addition, all of the contents of the Japanese Patent Application No. 11(1999)-250450 are incorporated into this specification by reference.

What is claimed is:

1. An image information reading apparatus comprising
a light source for generating a light beam,
photoelectric reading means for detecting intensity of incident light in a photoelectric manner,
a sample holding portion for holding a scanning target carrying certain image information,
an optical head which leads the light beam emitted by the light source to the scanning target placed on the sample holding portion so that the scanning target is irradiated with the light beam, and which leads induced light emitted by the scanning target in response to the irradiation thereon to the photoelectric reading means,
primary scanning means for moving the optical head in one direction with respect to the scanning target so that the scanning target is scanned in said one direction with the light beam led thereto by the optical head,
secondary scanning means for moving at least one of the sample holding portion or the optical head in another direction which is substantially orthogonal to said one direction, and
an optical element which is provided at a part on an optical path of the induced light between the optical head and the photoelectric reading means and which has a sufficient refractive power for collecting the induced light led toward the photoelectric reading means by the optical head, wherein
the secondary scanning means is capable of moving the optical head, and
the optical element comprises at least a first optical element to be moved together with the optical head by the secondary scanning means and a fixed second optical element.

2. An image information reading apparatus as defined in claim 1, wherein the optical element includes a lens with a positive refractive power, a parabolic mirror or a concave mirror.

3. An image information reading apparatus as defined in claim 1, wherein
the scanning target carrying the certain image information is a sample in which an organic substance marked with fluorescent dye is distributed,
the light beam is a beam of stimulating light which is capable of stimulating the fluorescent dye, and
the induced light is fluorescence from the stimulated fluorescent dye.

4. An image information reading apparatus as defined in claim 3, wherein the sample is any one of a gel-like supporting object, a membrane filter onto which the gel-like supporting object is transcribed, and an accumulation phosphor sheet.

5. An image information reading apparatus comprising
a light source for generating a light beam,
photoelectric reading means for detecting intensity of incident light in a photoelectric manner,
a sample holding portion for holding a scanning target carrying certain image information,
an optical head which leads the light beam emitted by the light source to the scanning target placed on the sample holding portion so that the scanning target is irradiated with the light beam, and which leads induced light emitted by the scanning target in response to the irradiation thereon to the photoelectric reading means,
primary scanning means for moving the optical head in one direction with respect to the scanning target so that the scanning target is scanned in said one direction with the light beam led thereto by the optical head,
secondary scanning means for moving at least one of the sample holding portion or the optical head in another direction which is substantially orthogonal to said one direction, and means for maintaining the induced light incident on said photoelectric reading means at a substantially uniform level regardless of a scanning position of said optical head, wherein said means for maintaining is provided in an optical path of the induced light between said optical head and said photoelectric reading means.

6. An image information reading apparatus as defined in claim 5, wherein said means for maintaining includes at least one of a lens with a positive refractive power, a parabolic mirror, and a concave mirror.

7. An image information reading apparatus as defined in claim 5, wherein the scanning target carrying the certain image information is a sample in which an organic substance marked with fluorescent dye is distributed, the light beam is a beam of stimulating light which is capable of stimulating the fluorescent dye, and the induced light is fluorescence from the stimulated fluorescent dye.

8. An image information reading apparatus as defined in claim 7, wherein the sample is any one of a gel-like supporting object, a membrane filter onto which the gel-like supporting object is transcribed, and an accumulation phosphor sheet.

* * * * *